United States Patent
Mahaffey et al.

(10) Patent No.: US 10,123,819 B2
(45) Date of Patent: Nov. 13, 2018

(54) MULTI-PIECE DERMATOME BODY

(71) Applicant: Zimmer Surgical, Inc., Dover, OH (US)

(72) Inventors: Mark Mahaffey, New Philadelphia, OH (US); Bruce Straslicka, Medina, OH (US)

(73) Assignee: Zimmer Surgical, Inc., Dover, OH (US)

( * ) Notice: Subject to any disclaimer, the term of this patent is extended or adjusted under 35 U.S.C. 154(b) by 133 days.

(21) Appl. No.: 14/686,125

(22) Filed: Apr. 14, 2015

(65) Prior Publication Data

US 2016/0302814 A1   Oct. 20, 2016

(51) Int. Cl.
  *A61B 17/50*   (2006.01)
  *A61B 17/322*   (2006.01)

(52) U.S. Cl.
  CPC .................. *A61B 17/322* (2013.01)

(58) Field of Classification Search
  CPC ........ A61B 17/322; A61B 2017/00544; A61B 2019/4868; A61B 17/50
  See application file for complete search history.

(56) References Cited

U.S. PATENT DOCUMENTS

| | | |
|---|---|---|
| 1,516,071 A | 11/1924 | Apolant |
| 1,594,613 A | 8/1926 | Hagen |
| 1,736,246 A | 11/1929 | Blair |
| 2,288,709 A | 7/1942 | Hood |
| 2,366,054 A | 12/1944 | Reese |
| 2,413,354 A | 12/1946 | Jenney |
| 2,419,114 A | 4/1947 | Briegel |
| 2,424,584 A | 7/1947 | Reese |
| 2,426,381 A | 8/1947 | Vermillion |

(Continued)

FOREIGN PATENT DOCUMENTS

| | | |
|---|---|---|
| CN | 107645935 A1 | 1/2018 |
| EP | 2532316 A2 | 12/2012 |

(Continued)

OTHER PUBLICATIONS

"International Application Serial No. PCT/US2016/027222, International Search Report dated May 30, 2016", 5 pgs.

(Continued)

*Primary Examiner* — Victor Nguyen
(74) *Attorney, Agent, or Firm* — Schwegman Lundberg & Woessner, P.A.

(57) ABSTRACT

A dermatome having a head, a neck, and a handle. The head of the dermatome may include a main housing at least partially defining a cavity and a removable member that may be configured to removably engage the main housing. The main housing may include one or more features configured to guide the removable member into alignment with the main housing and/or one or more features configured to engage the removable member. The removable member of the dermatome may be made from a different material than the main housing. The neck may include a first portion and a second portion, where the first portion is made from a different material than the second portion. The dermatome may be configured to connect to one or more of a fluid power source, a battery power source, and a wall power source.

21 Claims, 11 Drawing Sheets

(56) References Cited

U.S. PATENT DOCUMENTS

| | | |
|---|---|---|
| 2,428,018 A | 9/1947 | Eidam |
| 2,435,278 A | 2/1948 | Hood |
| 2,442,433 A | 6/1948 | Reese |
| 2,442,434 A | 6/1948 | Reese |
| 2,442,435 A | 6/1948 | Reese |
| 2,442,436 A | 6/1948 | Reese |
| 2,457,772 A | 12/1948 | Brown et al. |
| 2,479,185 A | 8/1949 | Reese |
| 2,479,260 A | 8/1949 | Reese |
| 2,484,740 A | 10/1949 | Reese |
| 2,579,029 A | 12/1951 | Barker et al. |
| 2,582,511 A | 1/1952 | Stryker |
| 2,590,299 A | 3/1952 | Douglas |
| 2,592,533 A | 4/1952 | Berkow |
| 2,636,495 A | 4/1953 | Arden |
| 2,643,579 A | 6/1953 | Jacoby, Jr. |
| 2,691,377 A | 10/1954 | Hood |
| 2,721,555 A | 10/1955 | Jenney |
| 2,730,100 A | 1/1956 | Hood |
| 2,730,102 A | 1/1956 | Hood |
| 2,787,272 A | 4/1957 | Groom |
| 3,037,509 A | 6/1962 | Schutz |
| 3,076,461 A | 2/1963 | Meek et al. |
| 3,076,462 A | 2/1963 | Meek et al. |
| 3,327,711 A | 6/1967 | Vallis |
| 3,428,045 A | 2/1969 | Kratzsch et al. |
| 3,613,242 A | 10/1971 | Hill et al. |
| 3,640,279 A | 2/1972 | Brown et al. |
| 3,670,734 A | 6/1972 | Hardy, Jr. |
| 3,776,236 A | 12/1973 | Brent |
| 3,820,543 A | 6/1974 | Vanjushin et al. |
| 3,857,178 A | 12/1974 | Stevens, II |
| 3,934,591 A | 1/1976 | Gleason |
| 4,038,986 A | 8/1977 | Mahler |
| 4,098,278 A | 7/1978 | Schwartz |
| 4,122,855 A * | 10/1978 | Tezel ............... A61B 17/322 606/131 |
| 4,690,139 A | 9/1987 | Rosenberg |
| 4,754,756 A | 7/1988 | Shelanski |
| 4,838,284 A | 6/1989 | Shelanski |
| 4,917,086 A | 4/1990 | Feltovich et al. |
| 5,873,881 A | 2/1999 | McEwen et al. |
| 6,080,166 A | 6/2000 | McEwen et al. |
| 6,530,931 B1 | 3/2003 | Rosenberg |
| 6,702,832 B2 | 3/2004 | Ross et al. |
| 8,002,779 B2 | 8/2011 | Barker et al. |
| 8,100,927 B2 | 1/2012 | Lucas et al. |
| 8,491,605 B2 | 7/2013 | Lucas et al. |
| 8,512,354 B2 | 8/2013 | Mahaffey et al. |
| 8,608,755 B2 | 12/2013 | Mahaffey et al. |
| 8,636,749 B2 | 1/2014 | Mahaffey et al. |
| 2012/0172894 A1 | 7/2012 | Sabir et al. |

FOREIGN PATENT DOCUMENTS

| | | |
|---|---|---|
| EP | 2545867 A1 | 1/2013 |
| EP | 2545868 A1 | 1/2013 |
| GB | 1048353 A | 11/1966 |
| WO | 1999062412 | 12/1999 |
| WO | 2009140980 A1 | 11/2009 |
| WO | 2013135177 A1 | 9/2013 |
| WO | 2014039609 A1 | 3/2014 |
| WO | WO-2016168255 A1 | 10/2016 |

OTHER PUBLICATIONS

"International Application Serial No. PCT/US2016/027222, Written Opinion dated May 30, 2016", 6 pgs.

"European Application Serial No. 16717809.4, Response filed Jun. 11, 2018 to Office Action dated Nov. 30, 2017", 14 pgs.

\* cited by examiner

MULTI-PIECE DERMATOME BODY

TECHNICAL FIELD

The disclosure is directed to dermatomes for surgically harvesting grafts of skin.

BACKGROUND

Conventional dermatomes are used for cutting skin tissue to obtain transplantable skin grafts. A skin graft is a patch of healthy skin that is harvested from one area of the body of a patient or donor site to cover a damaged or skinless area of the body of a patient. Typically, a dermatome has a front end holding a flat blade to be placed in contact with a tissue surface and a motor to oscillate the blade from side to side to create a slicing action which cuts the tissue as the dermatome is moved along the tissue surface.

SUMMARY

The disclosure is directed to several alternative or complementary designs, materials and methods of using medical device structures and assemblies. Although it is noted that conventional dermatomes exist, there exists a need for improvement on those devices.

Accordingly, one illustrative embodiment may include a dermatome having a handle and a head operatively coupled to the handle. The head may include a main housing and a removable member configured to removably engage the main housing at one or more engagement locations. The main housing may include a lower side for receiving a blade and an upper side at least partially defining a cavity. The removable member may be configured to engage the upper side of the main housing.

In some embodiments, the removable member may engage the upper side of the main housing at one or more engagement locations.

In some embodiments, the removable member may include one or more removable detents configured to removably engage one or more detents of the main housing to limit or prevent movement in one or more directions of the removable member relative to the main housing.

In some embodiments, engagement of the one or more removable detents of the removable member with the one or more detents of the main housing may prevent movement of the removable member is a first direction relative to the main housing.

Additionally, or alternatively, in some embodiments the removable member may include one or more feet configured to be received within one or more receivers of the main housing to limit or prevent movement in a second direction of the removable member relative to the main housing, where the first direction may be different than the second direction.

The above summary of some example aspects is not intended to describe each disclosed embodiment or every implementation of the claimed disclosure.

BRIEF DESCRIPTION OF THE DRAWINGS

The disclosure may be more completely understood in consideration of the following detailed description of various embodiments in connection with the accompanying drawings, in which.

Figure 1:
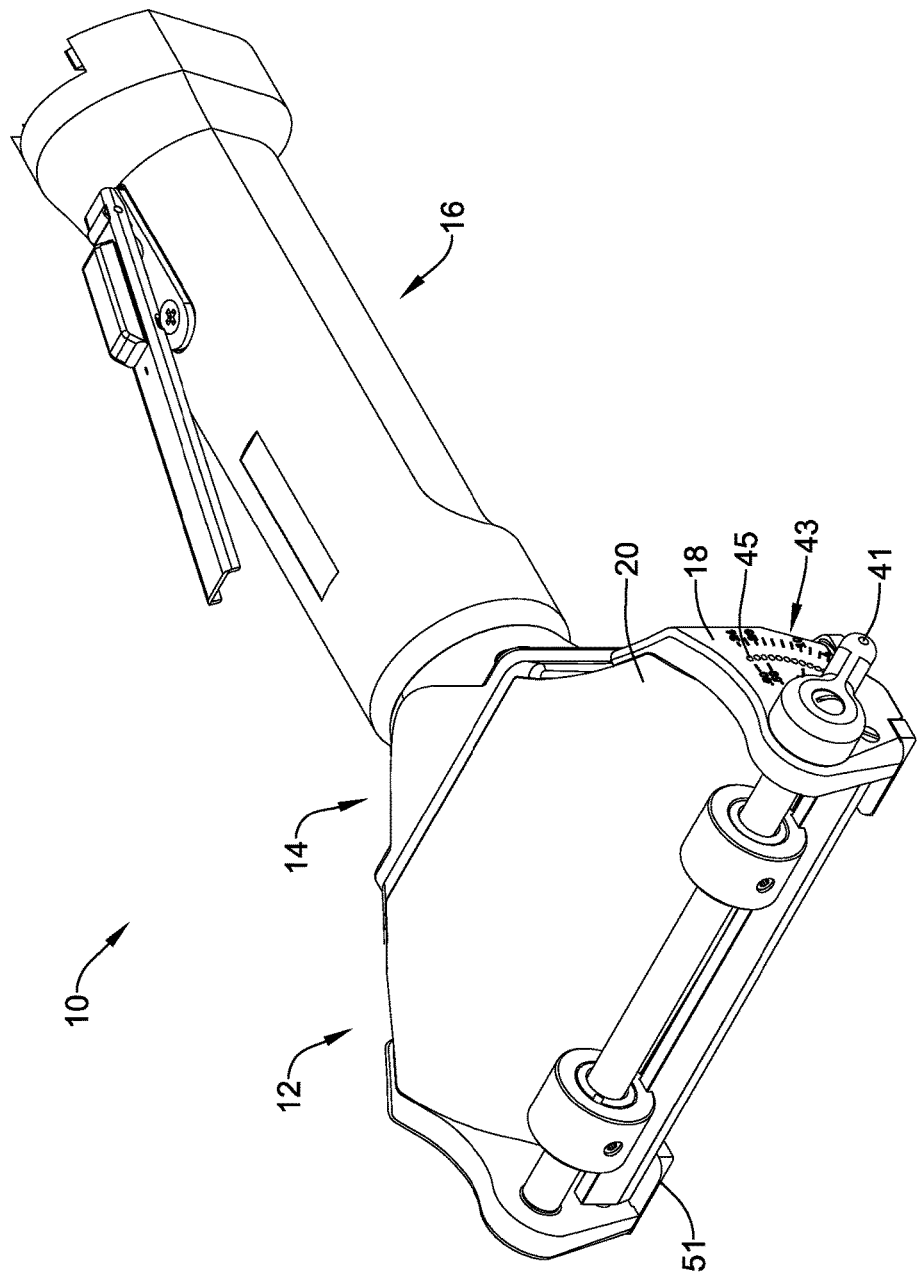
FIG. 1 is a perspective view of a dermatome according to an aspect of the disclosure.

While the disclosure is amenable to various modifications and alternative forms, specifics thereof have been shown by way of example in the drawings and will be described in detail. It should be understood, however, that the intention is not to limit aspects of the claimed disclosure to the particular embodiments described. On the contrary, the intention is to cover all modifications, equivalents, and alternatives falling within the spirit and scope of the claimed disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about", when referring to numeric values, generally refers to a range of numbers that one of skill in the art would consider equivalent to the recited value (i.e., having the same function or result). In many instances, the term "about" may be indicative as including numbers that are rounded to the nearest significant figure. Additionally, or alternatively, the term "about" may generally refer to the area around an object or to a first object positioned at least partially around a second object.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the claimed disclosure. The illustrative embodiments depicted are intended only as exemplary. Selected features of any illustrative embodiment may be incorporated into an additional embodiment unless clearly stated to the contrary.

Referring to FIG. 1, a dermatome 10 for harvesting grafts of skin tissue may have a head 12 operatively coupled or connected to a handle 16. The dermatome 10 may include a neck 14 connected to and intermediate the head 12 and the handle 16 or, instead, the neck 14 may connect directly to the head 12. The dermatome 10 may include a lower member 51 mounted on a lower side of the main housing 18 of head 12, where the lower member 51 may be configured to engage skin of a patient. The various portions of the dermatome 10 may be unitarily (e.g., monolithically) formed or formed from one or more parts interconnected in one or more manners. The parts, if more than one, forming the dermatome 10 may be interconnected using any connection technique, including, but not limited to screws, rivets, adhesives, threads, snap-fits, bayonet fittings, detents, friction fits, welds, magnets, and/or one or more other connection techniques.

Dermatome 10 may include a lever 41 or other mechanism for adjusting a depth at which the blade of the dermatome 10 engages skin of a patient. To facilitate understanding the depth at which the blade is to engage skin of a patient, the head 12 of the dermatome 10 may include indicia 43 indicating a depth at which the lever 41 and/or blade of the dermatome 10 is set. In some cases, the indicia 43 may indicate a measure and may be listed in one or more of metric units and English units. In one example, one side of the head 12 may list indicia in metric units and another side (e.g., a substantially opposite side) of the head 12 may list indicia 43 in English units. Thus, in some instances the other side of the head 12 may include an indicator (not shown), such as a pointer, that moves simultaneously with the lever 41 to provide an indicator for the indicia on the other side of the head 12 to facilitate indicating at which depth the lever 41 and the blade of the dermatome 10 are set. Alternatively, or additionally, the metric units and English units may be displayed on the same side of the head 12.

The main housing 18 of the head 12 may include one or more indentations 45 for engaging the lever 41. Such indentations 45 may facilitate locking the lever 41 and the blade at a desired depth for use. In one example, the indentations 45 may align with the different indicia 43 to facilitate indicating at which depth the lever 41 and the blade of the dermatome 10 are set.

Figure 2:
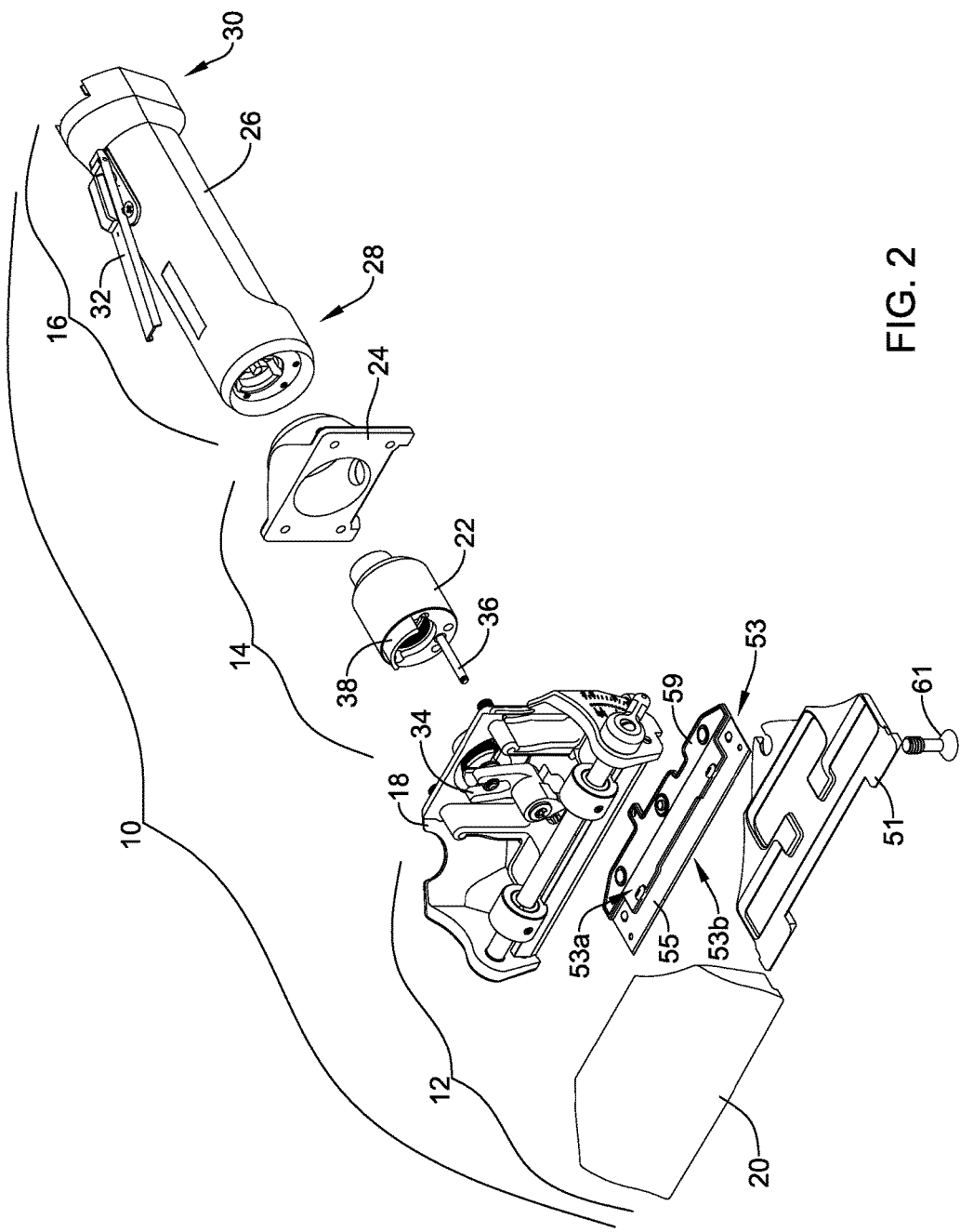
FIG. 2 is an exploded perspective view of a dermatome according to an aspect of the disclosure.

FIG. 2 is an exploded perspective view of an illustrative dermatome 10. Dermatome 10 may include a blade assembly 53 capable of being mounted on the main housing 18 of the head 12, as well as the lower member 51 capable of engaging a lower surface of the main housing 18. In some instances, the lower member 51 may be a width plate capable of controlling the width of skin tissue to be cut by a blade 55 of blade assembly 53. Dermatome 10 may include a set of lower members 51 (e.g., a plurality of width plates), where each width plate allows for a cut of tissue having a different width. Alternatively or in addition, dermatome 10 may include at least one adjustable lower member 51 (e.g., a width plate) capable of allowing various widths of tissue to be cut by blade 55, where the width plate may be adjusted by a user or other party to harvest a desired width of the skin tissue.

Blade assembly 53 may include the blade 55 and a blade mount 59, where the blade 55 and the blade mount 59 may be interconnected. The blade assembly 53 may be mounted on the main housing 18 by being fitted between the lower surface of the main housing 18 and the lower member 51 or may be positioned or mounted adjacent to the main housing 18 in any other manner known in the mounting art. Blade assembly 53 may be mounted to the main housing 18 so as to be fixed with respect to the main housing 18 or so as to allow the blade assembly 53 to move in at least side-to-side movement with respect to the main housing 18 (e.g., reciprocate).

Although the blade assembly 53 may be mounted to main housing 18 in any manner, dermatome 10 may include, for example, a system for mounting blade assembly 53 to the lower surface of main housing 18 utilizing the lower member 51 and screw 61 (or other connecting feature), as seen in FIG. 2. In the example, the blade assembly 53 may be positioned so as to have a first side 53a facing and/or contacting the lower surface of the main housing 18 and a second side 53b facing and/or contacting a first side of the lower member 51. The contact between the blade assembly 53, the main housing 18 and the lower member 51 may allow for movement of blade assembly 53 in at least first and second directions (e.g., side-to-side), while preventing up and down movement of the blade assembly 53.

The head 12 of the dermatome 10 may include a main housing 18 and a removable member 20 (e.g., a cover or other removable member) that may be removably connected to or engaged with the main housing 18 at or about an upper side thereof at one or more engagement locations. The main housing 18 may be made from one or more parts and the removable member 20 may be separately made of one or more parts. In one example, the main housing 18 may be monolithically formed and/or the removable member 20 may be monolithically formed.

The main housing 18 and the removable member 20 may be configured from the same material(s) or different materials. In one example, the main housing 18 may be at least partially configured from a metal and the removable member 20 may be at least partially configured from a polymer. In one instance, the main housing 18 may be monolithically formed of a metal, such as stainless steel, aluminum, or other metallic material, while the removable member 20 may be monolithically formed of a polymer material.

In some cases, the dermatome 10 may be configured out of a plurality of materials to facilitate a desired balancing of the dermatome 10 between the head 12, the neck 14, and/or the handle 16. Using a polymer for portions of the dermatome 10 may facilitate, along with other features of the dermatome 10, the use of a robust material yet relatively heavier material such as metal for other portions of the dermatome 10, while maintaining a desired balance along the dermatome 10. Other types of materials and/or techniques may be utilized to create a dermatome that is balanced as desired.

The neck 14 of the dermatome 10 may be a unitary structure or may be configured from one or more portions that fit together. In the example shown in FIG. 2, the neck 14 may include a first portion 22 and a second portion 24, where the first portion 22 may be inserted into the second portion 24 and into the head 12. The first portion 22 and the second portion 24 may be configured from the same material(s) or different materials. In one example, the first portion 22 of the neck 14 may be at least partially configured from a metal and the second portion 24 of the neck may be at least partially configured from a polymer.

The first portion 22 of the neck 14 may include or connect to a pin 36. When the neck 14 is connected to the head 12, the pin 36 may provide a pivot axis for a reciprocating mechanism 34 located within the head 12, where the reciprocating mechanism 34 may be configured to reciprocate the blade 55 of the dermatome 10 side-to-side in response to actuation of an actuator (e.g., actuator 32, as discussed below).

In some instances, the first portion 22 of the neck 14 may include a guard 38. The guard 38 may be configured on the first portion 22 of the neck 14 to block or guard against accidental interaction with the reciprocating mechanism 34 when the removable member 20 of the head 12 has been removed from connection with the main housing 18 of the head 12. The guard 38 may be unitarily (e.g., monolithically) formed with the first portion 22 of the neck 14 or connected to the first portion 22 so as to form a part of the first portion 22.

The handle 16 of the dermatome 10 may include a housing 26 having a first end 28 and a second end 30. The housing 26 may house or at least partially house various components for operating the dermatome 10 including, but not limited to one or more of a motor, a valve, electrical connections, and/or one or more other components that facilitate operation of the dermatome 10. The handle 16 may include an actuator 32 (e.g., a lever, a movable button, a touch sensitive button, or other actuator) that is configured to effect operation of the blade assembly 53 through activation of a motor (not shown) that engages the reciprocating mechanism 34 located in the head 12 and in engagement with the blade assembly 53. In one example, when the actuator 32 is engaged, the blade 55 of the blade assembly 53 may be in operation moving side-to-side, and when the actuator 32 is released or is being released, the blade may cease movement or slow its movement, respectively.

At or near the first end 28 of the housing 26, the handle 16 may be configured to engage the neck 14. In one example, the first end 28 of the handle 16 may be configured to receive at least some of a portion of the neck 14 within the first end 28 of the handle 16. When assembled together, the handle 16 may be connected to neck 14, for example, with screws (e.g., screws extending through the first portion 22 of the neck 14, the second portion 24 of the neck 14, and/or the housing 26 of the handle 16), threads, adhesives, and/or one or more other connectors.

At or near the second end 30 of the housing 26, the handle 16 may be configured to engage a power supply. In instances when the motor of the dermatome 10 is electrically powered, the handle 16 may be configured to receive an electrical connector in communication with an electrical power supply (e.g., wall power, a battery pack, or other electrical power supply). In instances when the motor of the dermatome 10 is powered by a fluid (e.g., air, or other gas or a liquid), the handle 16 may be configured to receive a nozzle of a mechanism for supplying a fluid to the dermatome 10 (e.g., a hose or other mechanism configured to supply fluid to the dermatome 10).

Example metals used to configure the various parts of the dermatome 10 may include, but are not limited to, aluminum, stainless steel, titanium, and other similar or dissimilar metals. In some cases, the metal(s) may be or include a metal capable of withstanding being submerged in a variety of environments spanning various pH levels, including, but not limited to, pH levels less than 12 (e.g., pH levels between 11 and 12, pH levels between 10 and 12, or pH levels between 9 and 12). Example polymers used to configure the various parts of the dermatome 10 may include, but are limited to, polyetheretherketone (PEEK), polyetherimide (e.g., Ultem® or other polyetherimides), polyphenylsulfone (PPSU), or other similar or dissimilar polymers. In some cases, the polymer(s) may be or may include a polymer that can withstand high temperatures without structurally changing. In one example, the dermatome 10 may include the main housing 18 of the head 12, the first portion 22 of the neck 14, and the housing 26 of the handle 16 configured partially or entirely from stainless steel or a different metal and the removable member 20 of the head 12 and the second portion 24 of the neck 14 configured partially or entirely from PEEK and/or a different polymer. Alternatively, or in addition, the main housing 18 of the head 12, the first portion 22 of the neck 14, and the housing 26, may be configured partially or entirely from PEEK or a different polymer and the removable member 20 of the head 12 and the second portion 24 of the neck 14 may be configured partially or entirely from stainless steel or a different metal.

Figure 3:
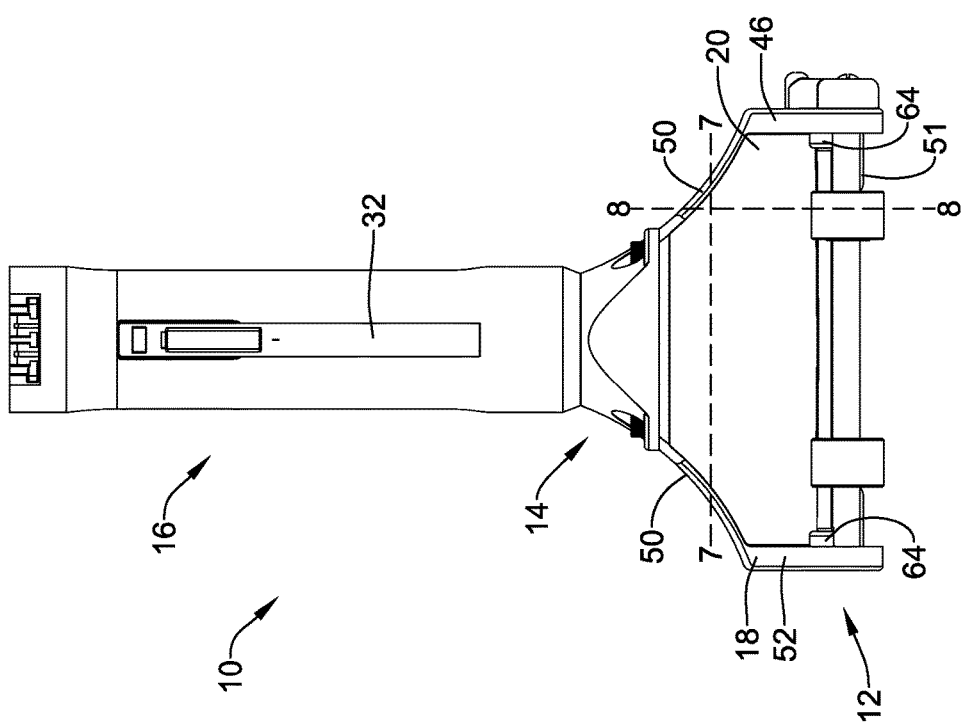
FIG. 3 is a top view of a dermatome according to an aspect of the disclosure.

FIG. 3 is a top view of the dermatome 10. As shown in FIG. 3, the removable member 20 may fit at least partially within a perimeter defined by walls 46 of the main housing 18. In some instances, the removable member 20 may overlay a portion or all of the top 52 (e.g. an upper edge) of the walls 46. Dotted lines 7-7 and 8-8 represent the lines about which cross-sections are taken and illustrated in FIG. 7 and FIG. 8, respectively.

Figure 4:
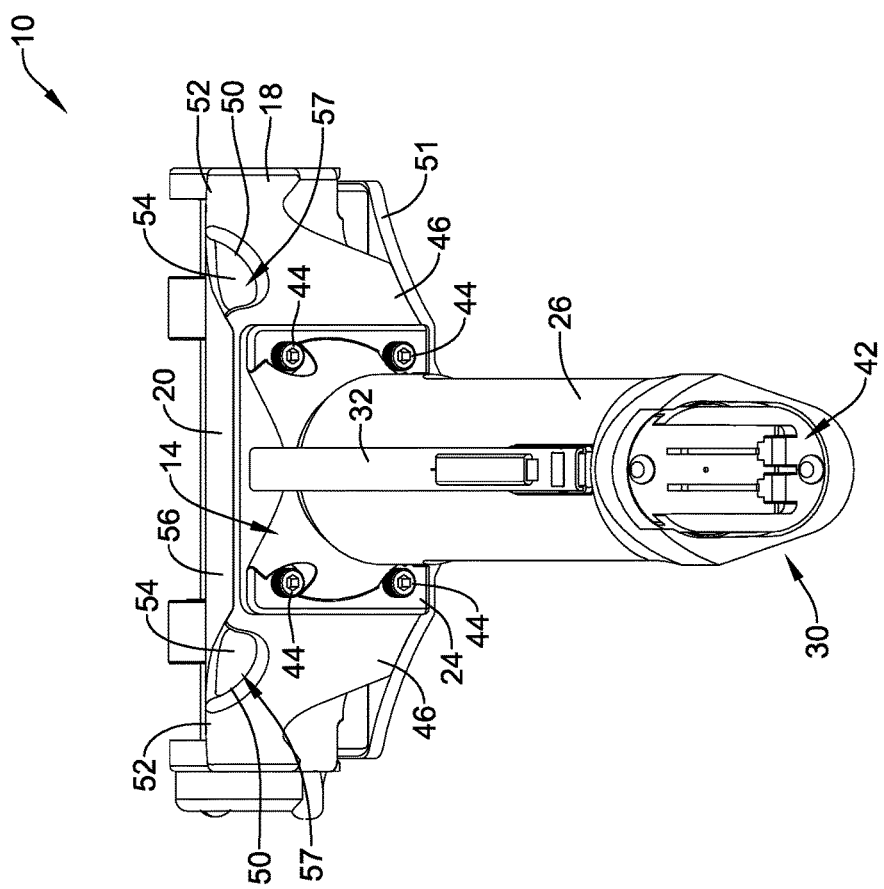
FIG. 4 is a perspective view from a back side of a dermatome according to an aspect of the disclosure.

FIG. 4 is a back side view of the dermatome 10. In FIG. 4, a connector 42 of the housing 26 of the handle 16 is shown. The connector 42 shown in FIG. 4 is configured to receive a connector of an electrical power supply to provide power to operate an electrical motor of the dermatome 10 and/or to power other electrical components, if any, of the dermatome 10.

The neck 14 is shown as connected to the head 12 in the illustrative dermatome 10 of FIG. 4. The neck 14 may be connected to the head 12 with screws 44 and/or with one or more other connectors/connection techniques. In some instances, the screws 44 and/or other connectors may be inserted through the second portion 24 of the neck 14 and into or through a wall 46 of the main housing 18, where the wall 46 may at least partially define a cavity 48 (see FIG. 5) in or at an upper side of the head 12.

The wall 46 of the main housing 18 may include one or more indents 50 configured to facilitate removal of the removable member 20. The indents 50 may be formed in the top 52 that extends along the wall 46 to allow a user's finger or a tool to be inserted under a portion or portions of the removable member 20 to facilitate disengaging the removable member 20 from the main housing 18 when a force is applied to the removable member 20 in a direction away from the main housing 18. In some cases, the removable member 20 may include an indent cover 54 that may extend from a top portion or wall 56 of the removable member 20 to close off the cavity 48 at one or more of the indents 50 from exterior the dermatome 10. The indents 50, the top wall 56 of the removable member 20, and the indent cover 54 may form gap 57 configured to receive a tool or a finger of a user to facilitate applying a force to the removable member 20 in a direction away from the main housing 18 to disengage the removable member 20 from the main housing 18. In some embodiments, the removable member 20 may be detached or removed from the main housing 18 without loosening and/or removing any fasteners, such as threaded fasteners of the dermatome 10. For example, attachment and detachment of the removable member 20 may be via a snap fit or interference fit between components of the removable member 20 and the main housing 18.

Figure 5:
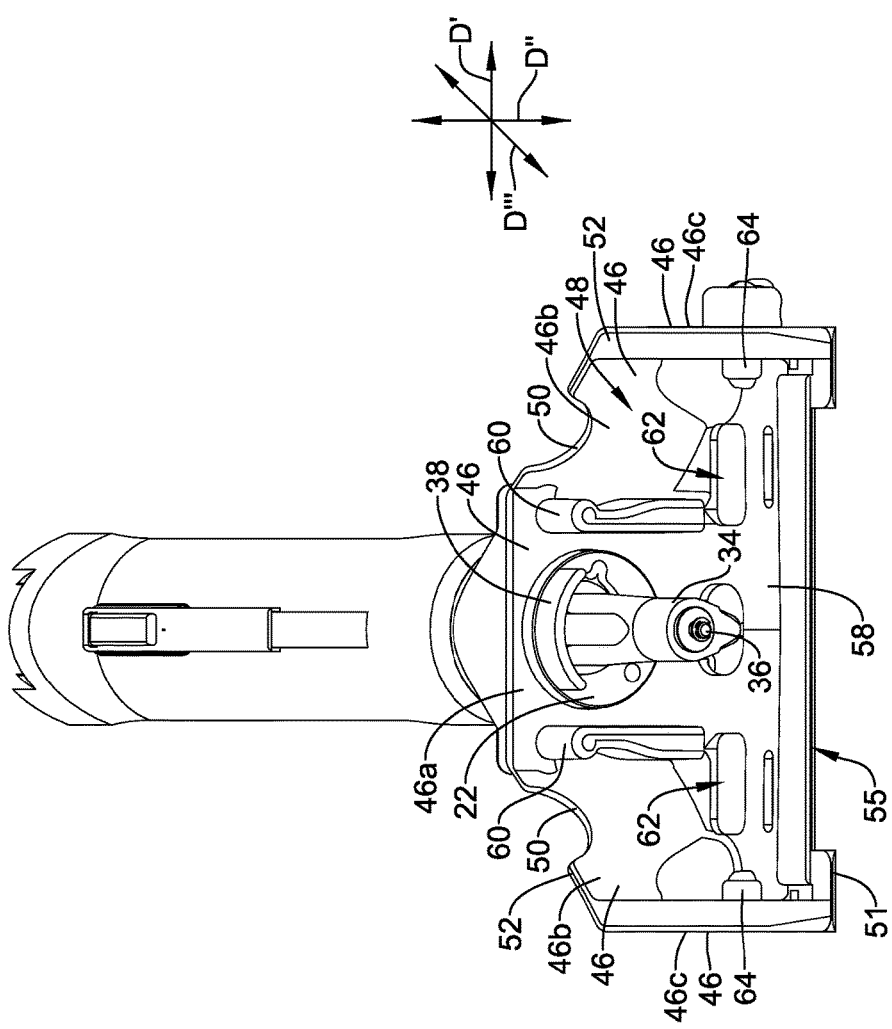
FIG. 5 is perspective view from a front side of a dermatome with a removable member removed according to an aspect of the disclosure.

FIG. 5 is a front perspective view of the dermatome 10 with the removable member 20 removed to show the interior or cavity 48 of the head 12. The main housing 18 of the head 12 may include one or more walls 46 extending from a base 58 to a top 52. In one example, the walls 46 may include a back wall 46a, one or more angled or corner walls 46b, and one or more side walls 46c, where each of the angled or corner walls 46b may extend between the back wall 46a and one of the side walls 46c. The base 58 and the walls 46 of the main housing 18 may at least partially define, along with the removable member 20, the cavity 48 of the head 12. The reciprocation mechanism 34 may be positioned within the cavity 48 of the head 12, and visible when the removable member 20 is removed from the main housing 18.

The main housing 18 may include one or more engagement features, such as one or more detents 60 (e.g., a first detent 60 and a second detent 60, as shown in FIG. 5) configured to engage one or more mating engagement features of the removable member 20. In some cases, the detents 60, or other engagement features, may be configured to prevent or limit movement of the removable member 20 with respect to the main housing 18 in at least a first direction D' (e.g., a side to side movement) and/or a second direction D" (e.g., a vertical or up and down movement).

The detents 60 may extend from one or more walls 46 and/or the base 58 of the main housing 18. As shown in FIG. 5, the detents 60 of the main housing 18 may extend from the back wall 46a and/or the base 58. In some instances, the detents 60 may receive screws 44 used to connect the neck 14 to the head 12. Alternatively, or in addition, the detents 60 may be formed by the screws or other connector connecting the neck 14 to the head 12.

One or more receivers 62 (e.g., a recess or other receiver) may be located in the base 58 of the head 12. The receiver 62 may be a recess in the base 58 facing or opening into the cavity 48 of the head 12 and may be configured to receive the removable member 20. In some instances, the receivers 62 may be sized to prevent or limit movement of the removable member 20 in a third direction D'" (e.g., back-to-front and/or front-to-back movement) that is substantially perpendicular to the first direction D' and/or the second direction D". Although first direction D', second direction D", and third direction D'" are shown in FIG. 5, these directions are depicted only for the purpose of showing the directions are perpendicular or substantially perpendicular to one another and are not necessarily shown to depict directions relative to the dermatome 10. Illustrative directions D', D", and D'" are shown relative to the dermatome 10 in FIGS. 7 and 8, respectively.

As shown in FIG. 5, the main housing 18 may include one or more guides 64. A guide 64 may facilitate aligning the removable member 20 with the main housing 18 as the removable member 20 is being connected to the main housing 18. In one example, the guide 64 may extend from one or more side walls 46c of the main housing 18, such that the guides 64 contact, abut, and/or engage the top portion or wall 56 (e.g., upper surface) of the removable member 20 to guide and/or position the removable member 20 into alignment with the main housing 18.

Figure 6:
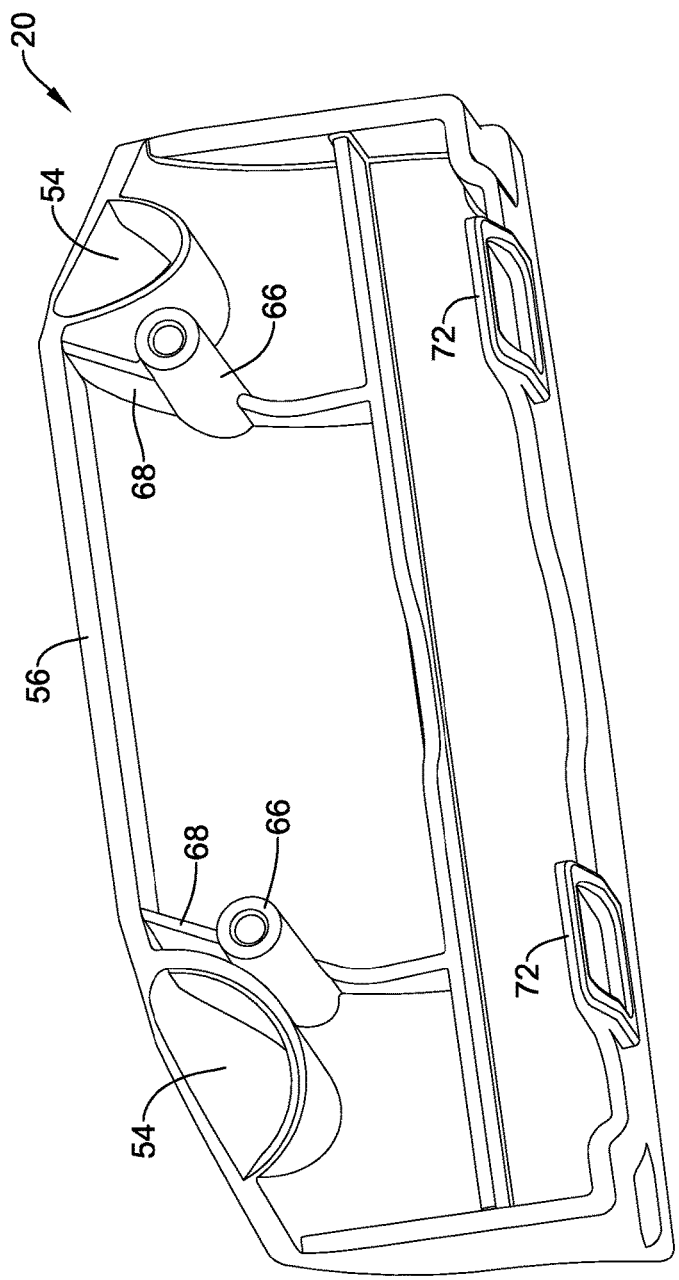
FIG. 6 is a perspective view from an underside of a removable member of a dermatome according to an aspect of the disclosure.

FIG. 6 is a perspective view of an underside of the removable member 20, where the underside of the removable member 20 may be the side that is facing an interior of the dermatome 10 and at least partially defines cavity 48 when the removable member 20 is engaging or connected to the main housing 18 of the head 12. The removable member 20 may include one or more features configured to facilitate engagement and/or disengagement with the main housing 18 including, but not required or limited to, one or more mating engagement features, such as detents 66 (e.g., a first detent 66 and a second detent 66, as shown in FIG. 6), one or more feet 72, and one or more indent covers 54. These features of the removable member 20 and others are described in greater detail below and with respect to other features of the dermatome 10.

Figure 7:
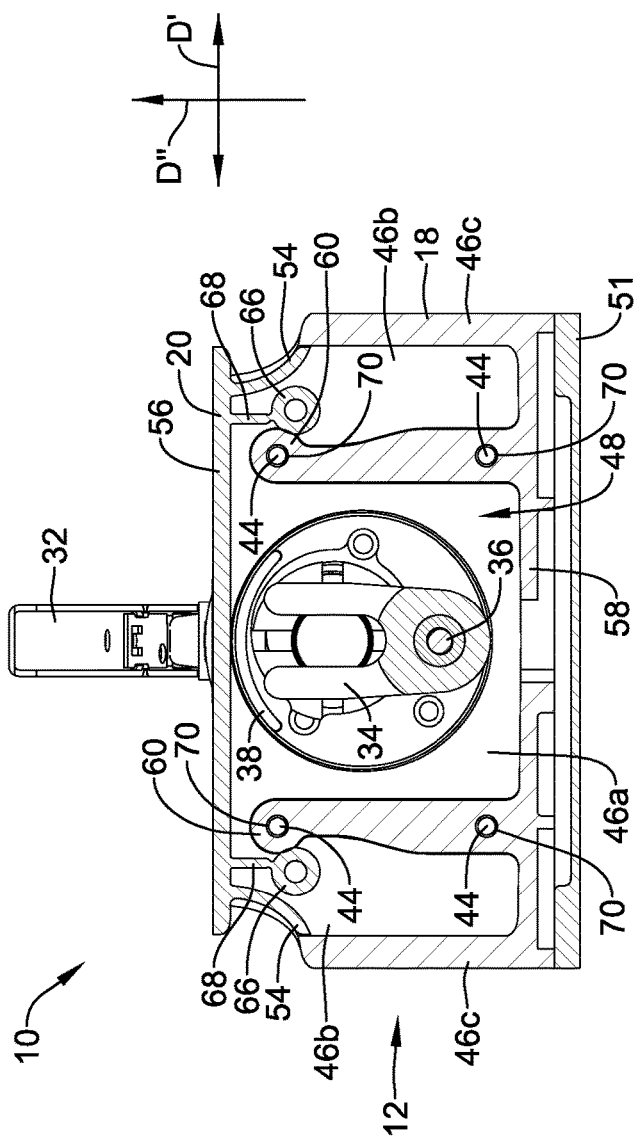
FIG. 7 is a cross-sectional view of a dermatome according to an aspect of the disclosure taken along line 7-7 of FIG. 3.

FIG. 7 is a cross-sectional view take along line 7-7 in FIG. 3, which depicts the cavity 48 formed by the main housing 18 and the removable member 20 of the head 12. The removable member 20 may include one or more engagement features, such as detents 66 (e.g., two detents 66, as shown in FIG. 7, or other number of detents 66), where the detents 66 or other engagement features may be configured to engage and/or abut the detents 60 or other engagement features of the main housing 18.

The detents 66 may be any shape and size configured to engage a detent 60 of the main housing 18. The detent 66 may have at least a portion with a generally circular or rounded cross-section as shown in FIG. 6, and/or the detent 66 may be configured such that it has a cross-section with one or more different shapes, where at least a portion of a shape of the cross-section of the detent 66 is formed and shaped to engage the detent 60. Although not required, the detent 66 may include or extend from a link 68 extending from the top portion or wall 56 or other portion of the removable member.

The detents 66 may extend from a portion of the removable member 20. In one example, the detents 66 may extend from or include a link 68 that extends from the top portion or wall 56 of the removable member 20, as shown in FIG. 6. Although the link 68 is shown in FIGS. 6 and 7 extending from the top portion or wall 56 of the removable member 20, the link 68 and/or the detent 66 may extend from one or more different portions of the removable member 20 including, but not limited to, the indent cover 54.

The detents 66 may be configured to flex as these features engage detents 60 of the main housing 18. In one example, the links 68 may be resilient and/or configured to flex to allow a portion of the detents 66 including a cross-section with a rounded portion or other portion configured to engage detents 60 to move around a rounded portion or other portion of detent 60 configured to engage the detent 66 and engage the detent 60 to at least partially removably connect or attach the removable member 20 to the main housing 18. The detents 66 may be configured to be resilient so as to be capable of flexing around detent 60 and then automatically return (e.g., bias) to or toward its natural position and secure the removable member 20 to the main housing 18 in a removable manner. Thus, the removable member 20 may be reversibly engaged and disengaged from the main housing 18 without loosening and/or removing any hardware (e.g., screws, nuts, bolts, etc.).

In some cases, a rounded cross-section portion of the detent 66 may be stiff relative to the links 68 so as to facilitate engagement of the removable member 20 with the main housing 18. Alternatively, or in addition, the rounded cross-sectional portion of the detent 66 may be resilient so as to flex around the detent 60 of the main housing 18 and resist detachment therefrom.

The detent 60 may be stiff relative to a resilient and/or flexible detent 66 to facilitate engaging the detent 66 and securing or attaching the removable member 20 to the main housing 18. For example, the detent 60, may be formed of a metal material as a unitary portion of the main housing 18, while the detent 66 may be formed of a polymer material as a unitary portion of the removable member 20. Alternatively or in addition to a portion of the detent 66 being resilient and/or flexible, a portion of the detent 60 may be resilient and/or flexible. In one example, the detent 60 may be configured to flex around a portion of the detent 66 and engage the detent 66 to facilitate attaching and/or connecting the removable member 20 with the main housing 18.

As discussed above, the engagement of the engagement feature of the removable member 20 (e.g., the detent 66) with the mating engagement feature of the main housing 18 (e.g., detent 60) may limit or prevent movement in one or more directions of the removable member 20 with respect to the main housing 18. In one example, the engagement of the detent 60 with the detent 66 may limit or prevent movement in a horizontal direction (e.g., first direction D') and/or vertical direction (e.g., second direction D") of the removable member 20 with respect to the main housing 18. Alternatively, or in addition, engagement of the detent 60 with the detent 66 may limit or prevent movement in one or more other directions, for example in a back-to-front direction or other direction, of the removable member 20 with respect to the main housing 18.

As discussed above, the detent 60 of the main housing 18 may extend from the base 58 and/or one or more walls 46 of the main housing 18. In some cases, for example when the detents 60 extend from the back wall 46a and/or in other cases, the detents 60 may include one or more bosses 70. As shown in FIG. 7, each of the one or more bosses 70 may be configured to receive a threaded portion of a screw 44 to facilitate securing the neck 14 to the head 12.

Figure 8:
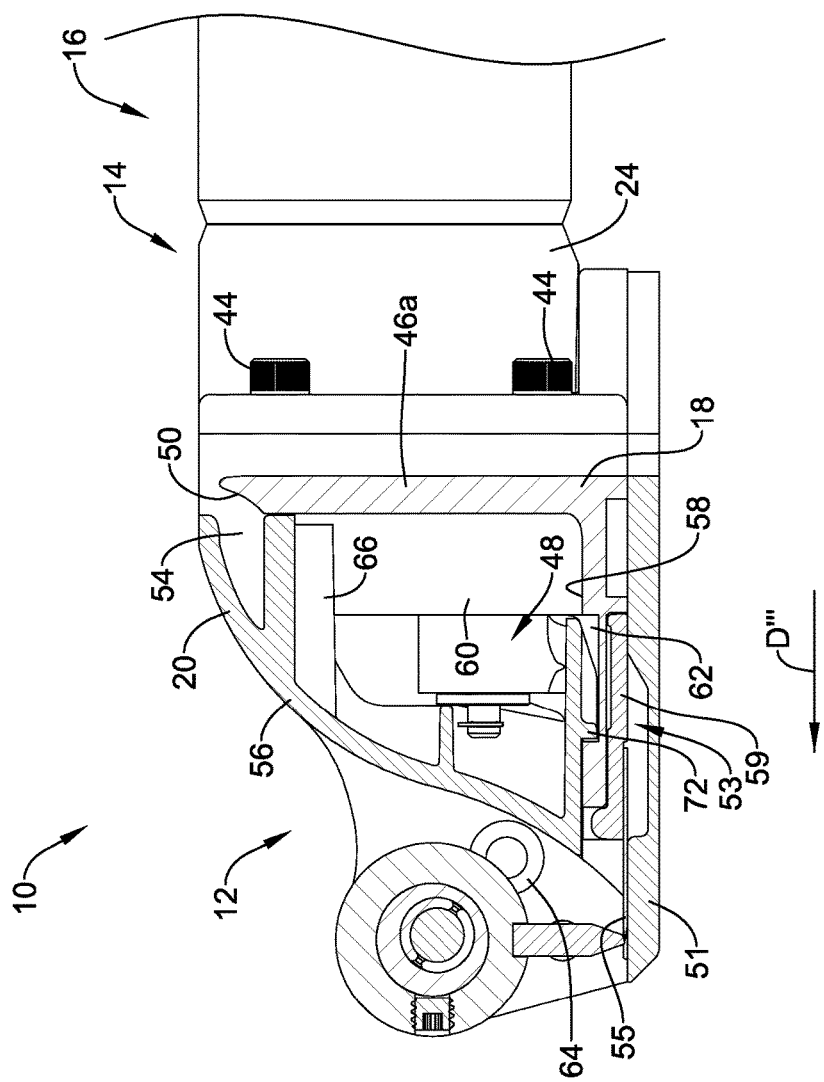
FIG. 8 is a cross-sectional view of a dermatome according to an aspect of the disclosure taken along line 8-8 of FIG. 3.

FIG. 8 is a cross-sectional view take along line 8-8 in FIG. 3, which depicts the cavity 48 formed by the main housing 18 and the removable member 20 of the head 12. As shown in FIG. 8, the removable member 20 may be guided into position by the top portion or wall 56 abutting the guides 64 to facilitate positioning the one or more feet 72 of the removable member 20 within the receivers 62 of the main housing 18.

The guides 64 may be configured to engage the top portion or wall 56 of the removable member 20. In some cases, the top portion or wall 56 of the removable member 20 may have an outer surface configured (e.g., curved, as shown in FIG. 8, or flat) to abut the guides 64, such that abutting the guides 64 may direct the removable member 20 into alignment with the main housing 18 for engagement therebetween. When the removable member 20 is engaging the main housing 18, the guides 64 may limit or prevent movement in the third direction D''' and/or a different direction of the removable member 20 with respect to the main housing 18.

The feet 72 of the removable member 20 may be configured to be received within the receivers 62 of the main housing 18. In one example, as the removable member 20 abuts the guides 64 to align the removable member 20 with the main housing 18, the feet 72 are aligned with the receivers 62 and may be positioned therein when the removable member 20 engages the main housing 18. Such positioning of the feet 72 within the receivers 62 may limit or prevent movement in the third direction D''' and/or other direction of the removable member 20 with respect to the main housing 18.

Figure 9:
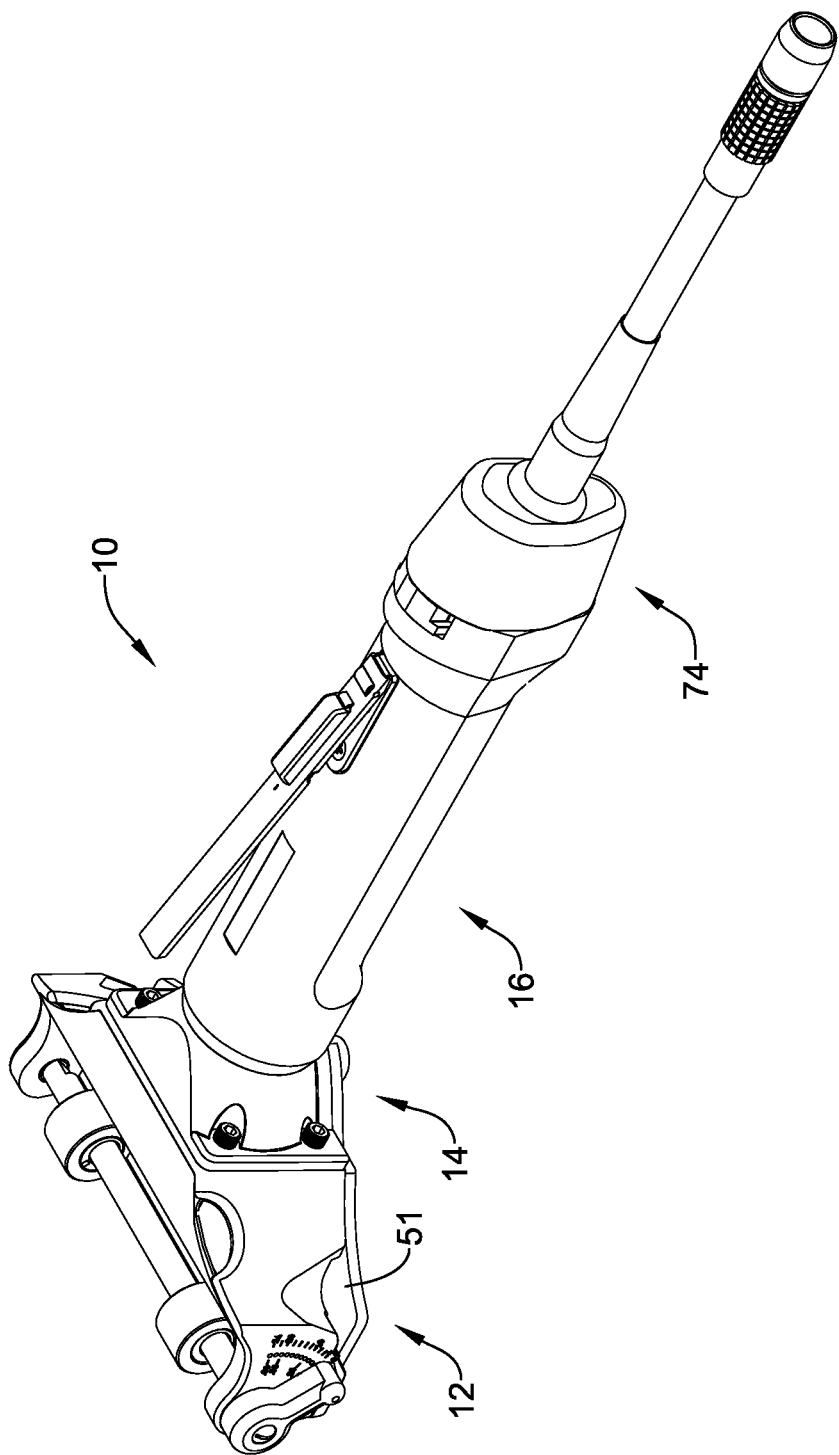
FIG. 9 is a perspective view of a dermatome according to an aspect of the disclosure.
Figure 10:
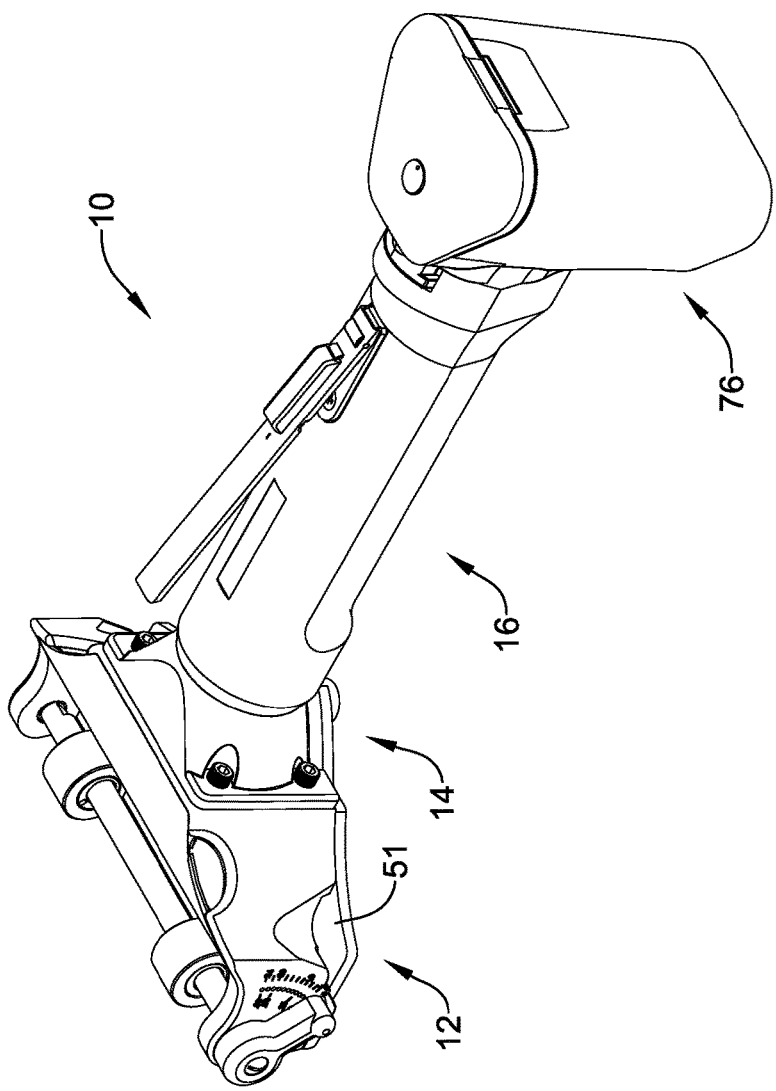
FIG. 10 is a perspective view of a dermatome according to an aspect of the disclosure.
Figure 11:
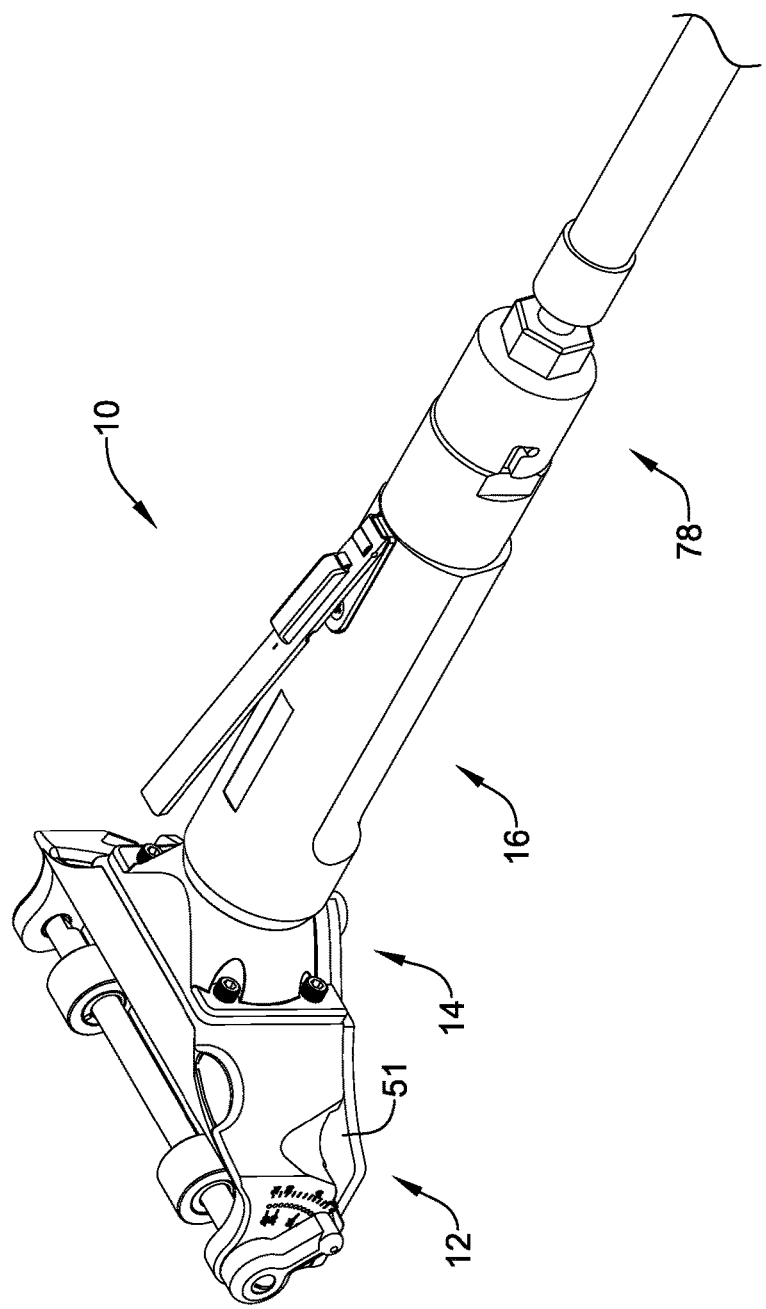
FIG. 11 is a perspective view of a dermatome according to an aspect of the disclosure.

FIGS. 9-11 depict dermatomes 10 having different power supply mechanisms. FIG. 9 depicts a dermatome 10 having a remote power connector 74 configured to connect to a supply of electricity from a wall power supply, a controller, or other remote power supply to the dermatome 10. FIG. 10 depicts a dermatome 10 having a battery pack connector 76 configured to connect a battery pack to the dermatome 10. Although it is not required, the electrical coupling interface of the battery pack connector 76 may be substantially similar to that of the remote power connector 74, which may allow for the connector 42 to connect to either the remote power connector 74 or the battery pack connector 76 and allow the dermatome 10 to be powered by a battery pack or a wall power supply, a controller or other remote power supply. FIG. 11 depicts a dermatome 10 having a fluid power connector 78 configured to connect a hose to the dermatome 10 to facilitate powering the dermatome 10 with a flow of fluid (e.g., a gas or a liquid).

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A dermatome comprising:
a handle; and
a head operatively coupled to the handle, the head including:
a main housing having a lower side and an upper side, the upper side defining a cavity;
a blade attachable to the lower side of the main housing;
a width plate configured to be mounted to the lower side of the main housing such that at least a portion of the blade is disposed between the width plate and the lower side, the width plate capable of controlling a width of skin tissue to be cut by the blade; and
a removable cover configured to removably engage the upper side of the main housing at one or more engagement locations.

2. The dermatome of claim 1, further comprising:
a detent of the main housing, the detent of the main housing is configured to engage the removable cover.

3. The dermatome of claim 2, wherein the removable cover includes a detent configured to engage the detent of the main housing, the detent of the removable cover is configured to flex when engaging the detent of the main housing.

4. The dermatome of claim 1, wherein the main housing includes an indentation in an upper edge of a wall defining the cavity, the indentation is configured to facilitate disengaging the removable cover from engagement with the main housing.

5. The dermatome of claim 1, wherein:
the main housing includes a base and one or more walls extending from the base to at least partially define the cavity; and
the base includes a receiver configured to receive the removable cover.

6. The dermatome of claim 5, wherein the removable cover includes a foot configured to engage the receiver in the base of the main housing.

7. The dermatome of claim 6, further comprising:
a guide extending from a wall defining the cavity of the main housing; and
wherein the guide is configured to guide the foot of the removable cover into engagement with the receiver in the base of the main housing.

8. The dermatome of claim 1, wherein the removable cover is configured from a first material and the main housing is configured from a second material different than the first material.

9. The dermatome of claim 1, wherein the removable cover is configured from a polymer material and the main housing is configured from a metal material.

10. The dermatome of claim 1, wherein:
the main housing includes a base and a plurality of walls extending from the base to at least partially define the cavity;
a first detent of the main housing and a second detent of the main housing extending from one or more walls of the main housing and the base, the second detent is spaced from the first detent; and
the removable cover includes a first detent configured to engage the first detent of the main housing and a second detent configured to engage the second detent of the main housing.

11. The dermatome of claim 1, further comprising:
a neck extending between the head and the handle, the neck having a first portion and a second portion separable from the first portion.

12. The dermatome of claim 11, wherein the first portion of the neck is configured from a first material and the second portion of the neck is configured from a second material different than the first material.

13. The dermatome of claim 1, wherein:
the upper side of the main housing includes a base and a plurality of walls at least partially defining the cavity, wherein the upper side includes a receiver in the base and a detent extending from one or more of the base and one of the walls at least partially defining the cavity; and
the removable cover includes a detent configured to engage the detent of the main housing and a foot configured to be received in the receiver of the base.

14. The dermatome of claim 13, further comprising:
a guide extending from a wall of the main housing, wherein the guide is configured to contact the removable cover and direct the foot of the removable cover into the receiver of the main housing.

15. The dermatome of claim 13, wherein the main housing is formed of a metal material and the removable cover is formed of a polymer material.

16. The dermatome of claim 13, wherein the main housing is monolithically formed of a first piece of material and the removable cover is separately monolithically formed of a second piece of material.

17. The dermatome of claim 13, wherein:
when the detent of the removable cover engages the detent of the main housing, the engagement is configured to prevent movement of the removable cover in a first direction relative to the main housing; and
when the foot of the removable cover is received in the receiver of the base, the receiver is configured to prevent movement of the removable cover in a second direction substantially perpendicular to the first direction relative to the main housing.

18. The dermatome of claim 1 wherein:
the main housing is formed of a metal material, the main housing further including:
a base;
a recess in the base;
a side wall extending from the base;
a rear wall extending from the base; and
a detent extending from one or more of the base, the side wall, and the rear wall; and
the removable cover is formed of a non-metal material and further includes:
a detent configured to engage the detent of the main housing to limit movement of the removable cover in a first direction relative to the main housing; and
a foot configured to be received in the recess of the base to limit movement of the removable cover in a second direction substantially perpendicular to the first direction relative to the main housing.

19. The dermatome of claim 18, further comprising:
a guide extending from the side wall of the main housing, the guide is configured to facilitate placement of the foot of the removable cover in the recess in the base of the main housing.

20. The dermatome of claim 18, further comprising:
a neck extending between the head and the handle, wherein:
the neck includes a first portion formed of a metal; and
the neck includes a second portion formed of a non-metal releasably connectable to the rear wall of the main housing and the second portion of the neck is configured to receive at least a portion of the first portion of the neck.

21. A dermatome comprising:
a handle; and
a head operatively coupled to the handle, the head including:
a main housing having a lower side for receiving a blade and an upper side defining a cavity, wherein the upper side of the main housing includes a base and a plurality of walls at least partially defining the cavity, and wherein the upper side includes a receiver in the base and a detent extending from one or more of the base and one of the walls at least partially defining the cavity;
a removable member configured to removably engage the upper side of the main housing at one or more engagement locations, wherein the removable member includes a detent configured to engage the detent of the main housing and a foot configured to be received in the receiver of the base; and
a guide extending from a wall of the main housing, wherein the guide is configured to contact the removable member and direct the foot of the removable member into the receiver of the main housing.

* * * * *